(12) United States Patent
Colone et al.

(10) Patent No.: US 6,443,981 B1
(45) Date of Patent: Sep. 3, 2002

(54) EXPANDABLE VASCULAR PROSTHESIS

(75) Inventors: William M. Colone; Kevin G. Farl, both of Phoenix; Barbara L. Teeter, Tempe; William L. Creer, Phoenix; Joseph B. Sinnott, Tempe, all of AZ (US)

(73) Assignee: Endomed, Inc., Phoenix, AZ (US)

( * ) Notice: Subject to any disclaimer, the term of this patent is extended or adjusted under 35 U.S.C. 154(b) by 0 days.

(21) Appl. No.: 09/574,870

(22) Filed: May 19, 2000

Related U.S. Application Data

(62) Division of application No. 09/244,343, filed on Feb. 4, 1999, now Pat. No. 6,187,054.

(51) Int. Cl.⁷ .................................................. A61F 2/06
(52) U.S. Cl. ..................................................... 623/1.13
(58) Field of Search ................................ 606/232, 144; 623/901, 1.1, 1.13, 1.27; 128/899, 898; 600/36

(56) References Cited

U.S. PATENT DOCUMENTS

| | | |
|---|---|---|
| 5,571,172 A | 11/1996 | Chin |
| 5,800,512 A | 9/1998 | Lentz et al. |
| 5,928,279 A * | 7/1999 | Shannon et al. ............... 623/1 |
| 6,001,125 A | 12/1999 | Golds et al. |
| 6,124,523 A * | 9/2000 | Banas et al. .................. 623/11 |

FOREIGN PATENT DOCUMENTS

| | | |
|---|---|---|
| WO | WO 95/05555 | 2/1995 |
| WO | WO 98/00090 | 1/1998 |
| WO | WO 98/27894 | 2/1998 |
| WO | WO 98/26731 | 6/1998 |
| WO | WO98/31305 | 7/1998 |
| WO | WO 98/31306 | 7/1998 |
| WO | WO 98/38947 | 9/1998 |
| WO | WO 99/32051 | 1/1999 |

* cited by examiner

*Primary Examiner*—Eduardo C. Robert
(74) *Attorney, Agent, or Firm*—David E. Rogers; Stuart A. Whittington; Squire, Sanders & Dempsey LLP

(57) ABSTRACT

A method is disclosed for making vascular prostheses from ePTFE said prostheses having a diameter which is larger, and a wall thickness which is smaller than previously achievable using ram extrusion techniques. The method consists of extruding a PTFE tube, finish processing the tube into an ePTFE tube, laterally dilating it by expansion in incremental steps, calendering the tube after each dilating step, while the tube is being maintained at an elevated temperature. Once the tube is dilated it can be sintered with another tube to form a laminate. Alternatively, a wire stent may be joined with one or more tubes, thereby biasing the laminate to a cylindrical configuration.

13 Claims, 6 Drawing Sheets

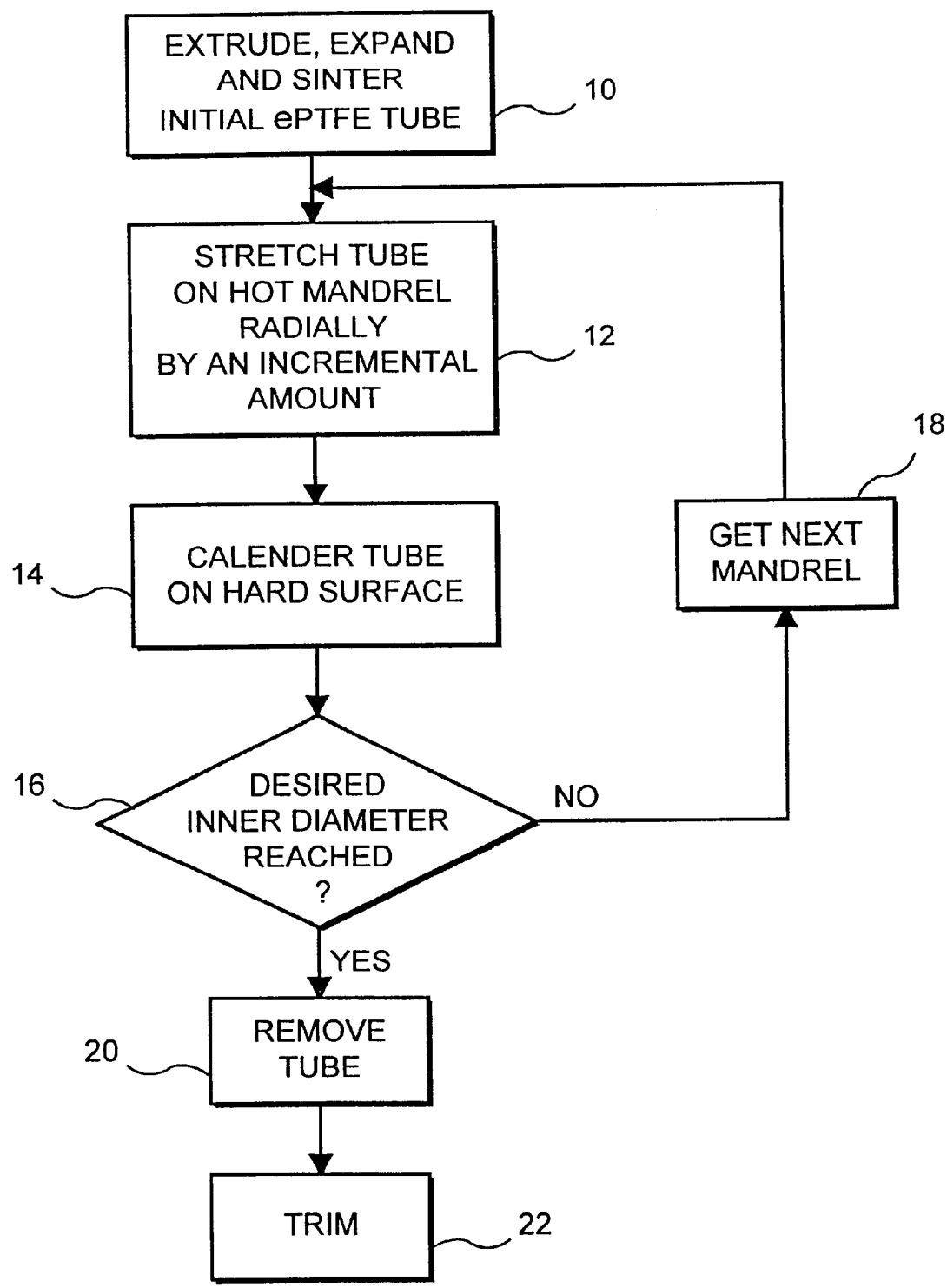
F I G. 1

EXPANDABLE VASCULAR PROSTHESIS

CROSS-REFERENCE TO RELATED APPLICATIONS

This is a divisional application of U.S. patent application Ser. No. 09/244,343 filed on Feb. 4, 1999, now U.S. Pat. No. 6,187,054.

BACKGROUND OF THE INVENTION

A. Field of Invention

This invention pertains to a method of making vascular prostheses from expanded PTFE (ePTFE) such as grafts and stent liners, said prostheses having an increased diameter, and a decreased wall thickness as compared to prior art grafts so that they can be used as a prosthesis in blood vessels having a relatively large diameter such as the aorta. More particularly, the invention pertains to a method of making a graft formed of at least one or more layers of ePTFE having an extremely thin wall yet high longitudinal tensile strength. A stent may be used in conjunction with the ePTFE layers, which allows the resulting prosthesis graft to be implanted without the use of a balloon or other graft expanding means.

B. Description of the Prior Art

Studies have shown tubes made of expandable polytetrafluorethylene (ePTFE) are ideally suited for various devices such as vascular prostheses. Vascular prostheses can be used to replace or repair blood vessels. Tubes made of ePTFE exhibit superior biocompatability, and can be made with a variety of diameters so that they can be implanted surgically.

Moreover, grafts of this type have high tensile strength in both the axial (or longitudinal) and radial direction so that the prostheses are very safe and do not dilate over time.

Grafts made of two layers of ePTFE or other plastic materials are well known in the prior art, illustrated by U.S. Pat. No. 5,800,512, PCT WO98/31305 and other references.

Generally, tubes for prior art ePTFE prostheses have been made using the following steps:

a. A PTFE resin is compounded with a lubricant (preferably a petroleum distillate, such as naphtha);

b. The compound is compacted under pressure;

c. The compacted mass is extruded into a tube using a standard ram extrusion process to its predetermined working diameter;

d. The tube is dried to remove the lubricant;

e. The dried tube is stretched longitudinally by up to 1000%;

f. The longitudinally stretched tube is sintered or cured at high temperature while its ends are fixed to insure that the tube does not shrink to its original length.

A problem with the process for manufacturing grafts in this manner is that there is a narrow range of reduction radios that produce acceptable results. The reduction ratio is the ratio of the cross-sectional area of the compacted mass to the cross-sectional area of the extruded material. If the reduction ratio is too low, the product will not have adequate strength for use as an implant. If the reduction ratio is too high, the pressure in the extruder will exceed safe manufacturing limits.

Large diameter prostheses with a wall thickness similar to that of natural vessel can be produced according to the prior art, but the resulting product is very weak because of the low reduction ratio. However, there is a need for strong, large diameter materials for surgical repair of larger vessels, such as the aorta. Furthermore, large diameter prostheses with thinner walls, which have more acceptable reduction ratios, are very difficult to produce according to the prior art because the extruded material is too fragile to be handled during the drying, expansion and sintering stages. However, there is a need for such large diameter, thin walled material for use in creating stent grafts for endovascular repair of large diameter vessels. Moreover, small diameter, thin walled material cannot be produced by the prior art because of the high reduction ratio of this material. This material is needed for creating stent grafts for endovascular repair of smaller vessels, including the carotid, femoral and renal arteries.

OBJECTIVES AND SUMMARY OF THE INVENTION

Accordingly, it is an objective of the present invention to provide a method of making ePTFE prostheses with relatively large diameters and/or thin walls as compared to prior art prostheses.

A further objective is to provide composite prostheses made of at least two layers of a plastic material, such as ePTFE, using the inventive method.

Yet a further objective is to provide a high strength graft suitable for a stent liner.

Yet a further objective is to provide a composite device combining the high strength material with a stent.

Other objectives and advantages of the invention shall become apparent from the following description.

Briefly, a prosthesis particularly suitable for vascular reconstruction and repair, is made by first extruding an initial PTFE tube by using a ram extruder and expanding and sintering it according to the prior art. The resulting initial tube having a diameter of less than about 8 mm. is then dilated radially. The process of dilation involves expanding the tube radially by small, incremental amounts under controlled conditions until a preselected diameter is obtained. Each radial expansion is followed by calendering the tube. This process of progressive radial dilation and calendering results in a thin walled tube with exceptional strength. When the tube is heated to about 200° C., it contracts slightly to a smaller diameter.

Using this process, two or more tubes made in the manner described may be superimposed and sintered together. First, the inner tube is placed over an appropriately sized mandrel. A second, slightly oversized tube is then placed over the first. The two tubes are than heated at approximately 200° C., causing the inner tube to conform tightly to the mandrel, and the outer tube to contract tightly about the inner tube. The tubes, still on the mandrel, can then be sintered at high temperature to cause them to adhere to each other. In one embodiment, the laminate thus formed is used as a stent liner. In another embodiment, a stent graft is formed by inserting one or more stents between the tubes prior to sintering.

In this application, the preferred stents are made of a material exhibiting martensitic characteristics, such as Nitinol (a nickel—titanium alloy). For example, a nitinol wire can be formed into open or closed circumferential loops defining a cylindrical shape. The cylindrical shape has a stent diameter which is normally larger than the diameter of the graft when the stent is free standing. When the stent is encapsulated in the graft, it is stressed radially inward. As a result, the stent graft is biased toward a cylindrical configuration having a diameter defined by the diameter of the tubes.

This type of stent graft is first introduced into a narrow sheath having a size between 6 and 20 French. The sheath is then inserted into the desired blood vessel, the device is ejected into the vessel, and because of the biasing imparted to it by the stent, the graft opens toward its original shape, thereby engaging the sidewalls of the respective blood vessel. Stent grafts of this type are particularly useful in vessels subject to external compression, such as the femoral or carotid artery, since the device will return to its original shape after the compressive force is removed.

In addition, a single tube produced according to this method can be used to produce a stent graft. First, a stent is placed over an appropriately sized mandrel. A slightly oversized tube is then placed over the stent. The stent and tube are then heated at approximately 200° C., causing the tube to contract tightly about the stent.

In this application, the preferred stents are made of a plastically deformable material such as stainless steel. For example, a stainless steel wire can be formed into open or closed circumferential loops defining a cylindrical shape. The cylindrical shape has a small compressed diameter but a larger expanded diameter.

This type of stent graft is positioned on a balloon catheter prior to insertion in the patient. The balloon catheter, or other expansion means, with the superimposed stent graft, is introduced into the patient by means of a narrow sheath having a size of 6 or 7 French. The balloon catheter is advanced to the delivery site, and the balloon is inflated. The stent graft opens to its expanded shape and is plastically deformed, thereby engaging the sidewalls of the respective blood vessel. Stent grafts of this type are particularly useful in smaller vessels, such as coronary arteries, since the smaller diameter of the device at introduction is critical for its clinical usefulness. Such stent grafts are also useful when the final expanded diameter of the stent graft is not precisely known prior to implantation.

BRIEF DESCRIPTION OF THE FIGURES

FIG. 1 shows a flow chart for forming an intermediate ePTFE tube which has been radially stretched;

FIGS. 8A–8E show a method of making a graft with two tubes and a stent in between.

DETAILED DESCRIPTION OF THE INVENTION

The inventive method and general types of vascular prostheses obtained by the subject method shall now be described in conjunction with the drawings. Referring to FIG. 1, the subject method includes several stages.

The first stage illustrated in FIG. 1 as step 10 of the process is to extrude, expand and sinter an initial tube from a PTFE resin to form an expanded PTFE tube. This step 10 includes the process inclusive of steps a–f described above and since the process is well known in the art, it will not be described any further. The initial ePTFE tube may have a nominal diameter of 6 mm, and an axial length of 6" and a thickness of about 0.5 mm. Depending on the final product, initial tubes of other diameters, and thicknesses may be made by the same process. The axial length of the initial tube is not critical since the final tube is trimmed anyway.

Next, a dilation stage is performed on this initial tube comprising several repetitive steps 12–18. During this dilation stage, the initial tube resulting from the extrusion stage 10 is gradually expanded radially until a preselected inner diameter is achieved.

More particularly, in step 12, a mandrel having an outer diameter slightly larger (for example 9 mm) than the initial tube is inserted therein.

Figure 2:
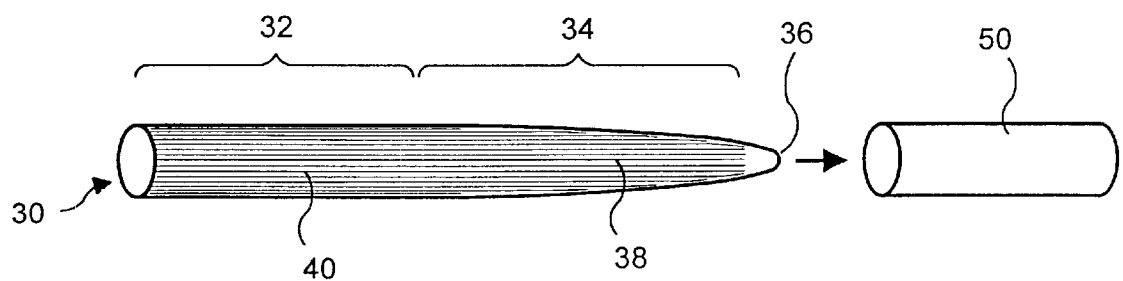
FIG. 2 shows a first type of mandrel used to make the intermediate tube.

In the subject process two different types of mandrels are used. FIG. 2 shows a first such mandrel 30. Mandrel 30 has two axially extending portions. The first portion 32 has a cylindrical shape, while the second portion 34 is somewhat conical or tapered. This second portion 34 terminates in a blunt tip 36.

Mandrel 30 may be for example about 18" long with section 32 being about 7" long and portion 34 being about 11" long. Preferably, mandrel 30 is made of stainless steel or similar material and is solid so that it has a high heat retention characteristic.

Importantly, the mandrel 30 has an outer surface 38 which is not perfectly smooth, but instead it has been scored with a plurality of microscopic scratches 40 oriented longitudinally. These scratches 40 may be applied by a fine sand paper, steel wool, or another similar abrasive or by machining.

It should be understood that a whole family of mandrels 30 are used, with increasing maximum diameters. For example, the narrowest mandrel 30 may have a diameter of about 9 mm, the next mandrel may have a diameter of 12 mm, and so on.

Figure 3:
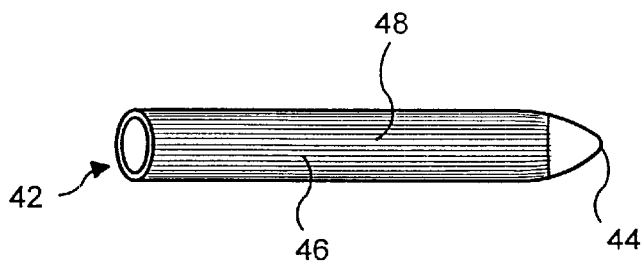
FIG. 3 shows a second type of mandrel used in the subject inventive process.

A second type of mandrel being used in the subject process is a mandrel 42. Mandrel 42 is also made of steel but rather than being solid, it is tubular, as seen in FIG. 3. Moreover, mandrel 42 has a substantially constant diameter. At one end, mandrel 40 is provided with a removable somewhat dome-shaped cap 44. Cap 44 is used to facilitate inserting the mandrel into the ePTFE tubes as discussed below. Importantly, mandrel 42 also has an outer surface 46 with microscopic scores or scratches 48.

Figure 4:
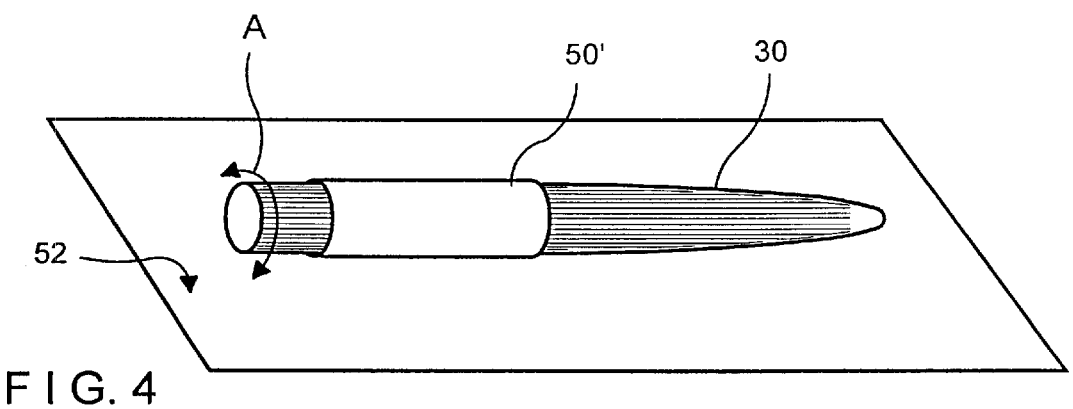
FIG. 4 shows the intermediate tube being calendered.

Referring back to FIG. 1, in step 12, a mandrel 30 is heated to about 50° C. and then its tip 36 is inserted into the initial tube 50, as shown in FIG. 2. The initial tube 50 is then pulled smoothly over the mandrel 30, first passing over portion 34 and then onto portion 32, to the position shown in FIG. 4. In this manner the diameter of initial tube 50 is increased smoothly and incrementally to a new value. For instance, tube 50' in FIG. 4 has a diameter of 9 mm.

Initially, it was found that expanding the tube radially using mandrels with a highly polished surface 38 was not very successful because, in many instances, the tube would split axially and had to be discarded. However, this problem was eliminated by using mandrels 30 with scored surfaces. These scores facilitate expanding the tube radially without tearing the same by reducing the amount of contact area between the tube and the mandrel.

Once the tube is positioned over section 32 of mandrel 30, the mandrel 30 and tube 50' are placed on a hard smooth surface 52 (made for example, from marble or other similar flat surface) and then calendered (step 14).

It should be noted that the process of increasing the diameter of tube 50' takes only a very short time (in the range of a few seconds). Accordingly, the mandrel 30 is still hot (i.e., about 50° C.) during the calendering step 14 and keeps the tube 50' hot as well. Calendering consists of rolling the tube 50' across surface 52 several times while pressing downward on the ends of mandrel 30 to form a pressure nip between the mandrel 30 and surface 52 with the tube 50' disposed in said nip. Each rotation indicated by arrows of the calendering step is sufficiently long to insure that the entire tube 50' passes through the nip to insure that the tube is evenly treated. This hand calendering process may also be automated and performed mechanically by loading each mandrel into a machine (not shown) which accomplishes substantially the same effect by generating a press nip.

Figure 5:
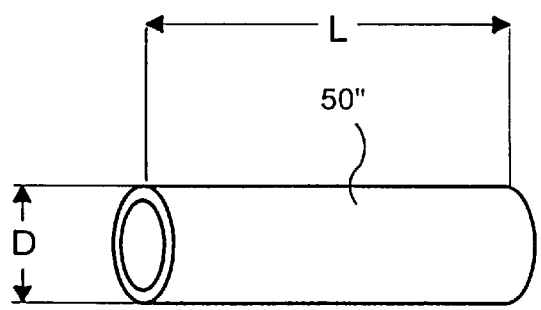
FIG. 5 shows a perspective view of the intermediate tube resulting from the process of FIG. 1.

After the calendaring step 14, the tube 50' is removed from the mandrel 30. Steps 12 and 14 are repeated several times with larger and larger heated mandrels 30 (step 18) until a tube 54 is obtained which has a desired or targeted inner diameter (step 16), as determined by the last mandrel 30 used. At this point, the tube may be removed (step 20) and trimmed axially to a desired length L (step 22) as shown in FIG. 5. Importantly, by this gradual dilation process, intermediate tubes 54 can be obtained having diameters D much larger and wall thickness much smaller than obtainable by previous methods. More specifically, the inventors were successful in making tubes having diameters of up to 25 mm or more with wall thickness less than 0.006". In general, it is expected that by using this method, tubes can be expanded radially by factors of up to ten. Tubes having a diameter of 25 mm or more and a wall thickness of less than 10 thousandths of an inch are virtually impossible to make by the standard ram extrusion process discussed above because the material would be too fragile to handle.

The radially expanded tube resulting from steps 10–16 is used as a building block to make several types of prostheses, such as a graft with an encapsulated stent, a stent liner, etc.

Figure 6:
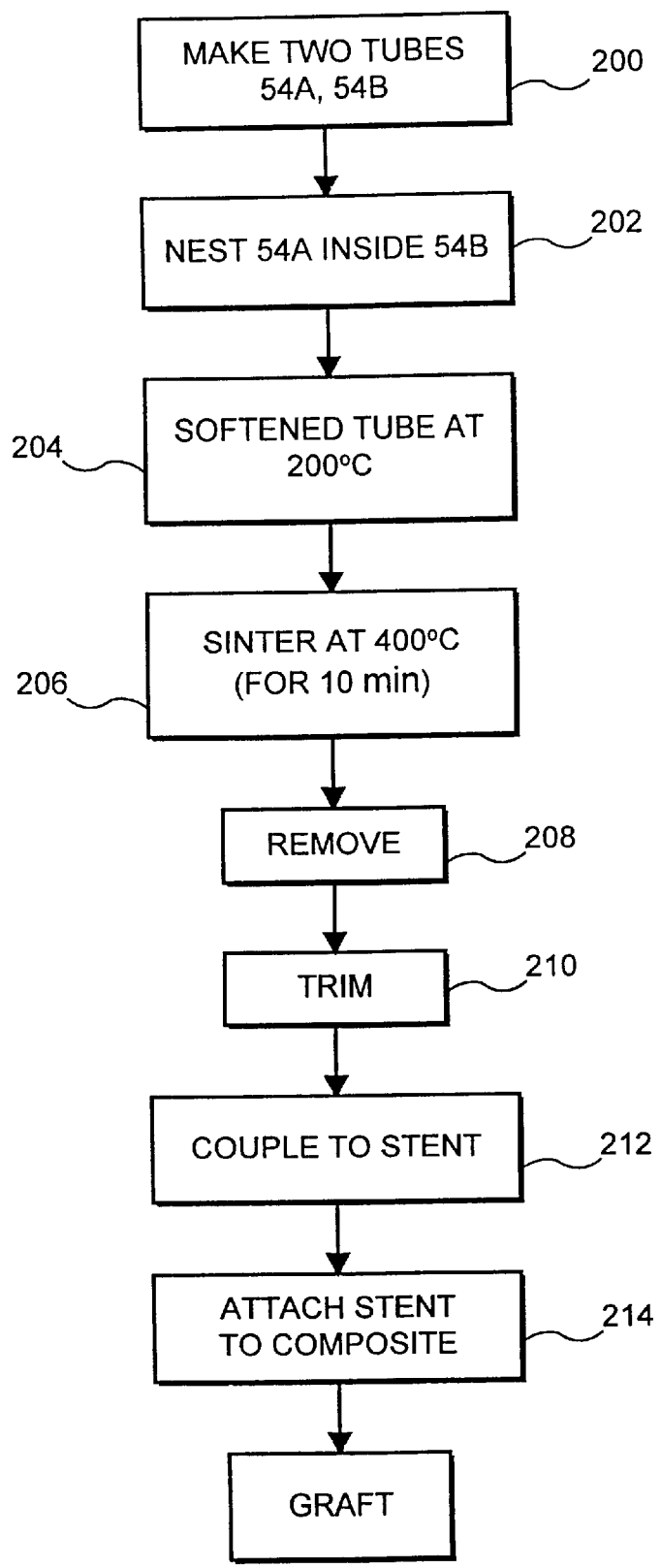
FIG. 6 shows the steps required to make a two layered laminated graft, using the intermediate tube of FIG. 5.
Figure 7A:
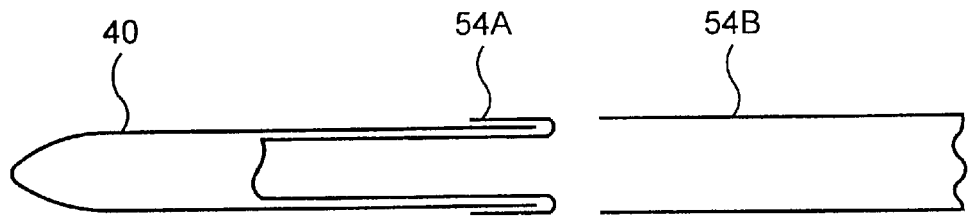
FIGS. 7A–7C show a method of superimposing two tubes having the same cross-sectional dimensions.
Figure 7B:
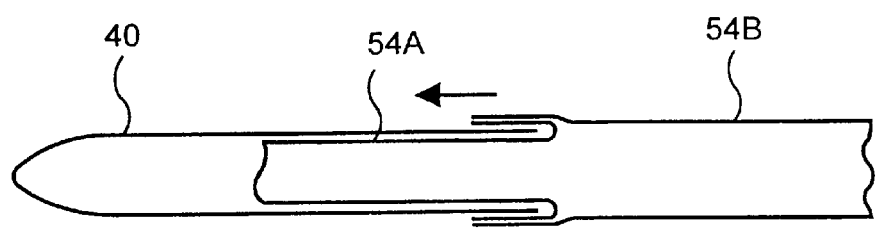
Figure 7C:
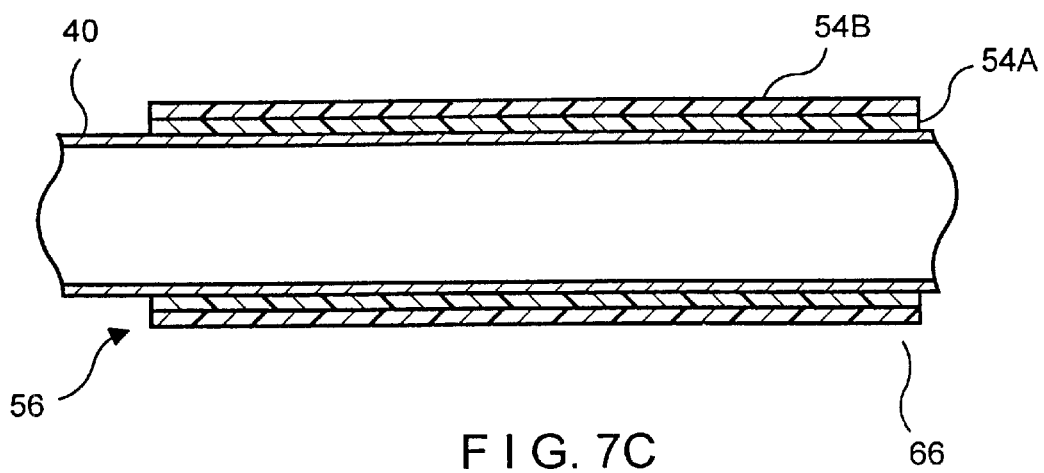

For example, a two layered laminated graft is made as follows. Referring to FIG. 6, in step 200 two intermediate tubes are made using the process of FIG. 1. Next, in step 202, the two intermediate tubes 54A, 54B are nested inside the other so that they are substantially coextensive on a mandrel 40. One technique for disposing one intermediate tube inside another is shown in FIGS. 7A–7C. First, tube 54A is partially pulled over mandrel 40 so that a length of about ½" is disposed on the end of mandrel 40. The rest of tube 54A is tucked inside the mandrel, as seen in FIG. 7A.

Next, as shown in FIG. 7B an axial portion of tube 54B is pulled over the portion of tube 54A resting outside the mandrel 40. The two tubes are then grasped together and pulled over the mandrel 40 and position over a mid-section thereof, as seen in FIG. 7C.

Next, in step 204 the mandrel of FIG. 7C is inserted into an oven preheated to about 200° C. for about two minutes. This heating causes the tubes to soften, radially contract, and to lightly adhere to each other, and to mandrel 40. As a result, the tubes do not have to be restrained longitudinally. Next, in step 206, the mandrel and two tubes are sintered in an oven at about 360° C. for about 10 minutes. This step causes the tubes to be set to their final geometric shape and to cure together as a laminate.

Next, in step 208, the tubes and mandrel are removed from the oven and allowed to cool to room temperature. Once cooled, the laminated tube is then removed from the mandrel, and in step 210, it is trimmed to the desired length.

Figure 7D:
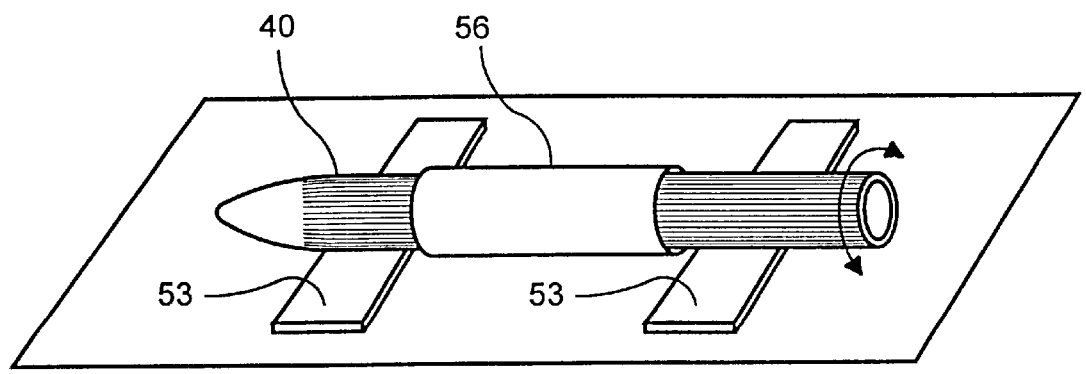
FIG. 7D shows a mandrel and shims used to reduce the thickness of a laminate.
Figure 7E:
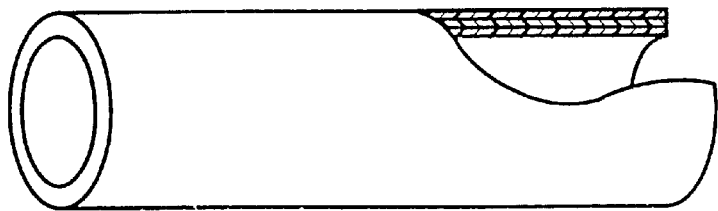
FIG. 7E shows a cross-sectional view of a three layer prosthesis constructed in accordance with this invention.

Typically, at this point the laminated tube has an outer diameter of about 20–40 mm and a thickness of about less than 10 thousandths of an inch. If desired, the thickness of the laminate may be reduced as follows. The mandrel 40 with the laminated tube 56 is placed on straight hard surface 52 on which two metallic shims 53 have been placed, as shown in FIG. 7D. The shims have a thickness equal to the desired final thickness of the laminated tube 56, and are placed in parallel at a distance which is larger than the length of the laminated tube 56. The mandrel 40 is positioned with the laminated tube 56 disposed between the shims 53. The mandrel 40 is then rolled over the surface 52 several times while a pressure is exerted downward on the ends of the mandrel 40. This action causes the tube 56 to be pressed radially inward by the press nip between the mandrel 40 and surface 52. The rolling action is continued until the surface of the mandrel 40 comes into contact with the shims 53, at which point the desired thickness for tube 56 has been reached.

This laminated tube 56 has very desirable characteristics which make it ideally suited for a variety of application, such as, for instance, a stent liner or cover. A stent made of a metallic wire, or other material is coupled either inside or outside the composite tube (step 212). The stent is then secured to the laminated tube 56, for example with sutures (step 214) resulting in a prosthesis which can be used for example as a percutaneous intravascular graft inside the aorta.

If necessary, the liner can be made from three layers using the process described above. One such liner is shown in FIG.

Figure 7F:
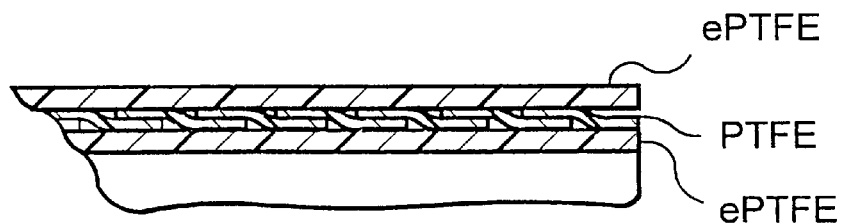
FIG. 7F shows a cross-sectional view of a prosthesis made of two tubular members and a wound tape therebetween.

7E. Alternatively, the middle layer of the liner can be formed from PTFE tape wrapped in a spiral pattern about the inner tube as shown in FIG. 7F. The resultant liner is formed of an inner and an outer layer of ePTFE and a central layer of PTFE.

Tests have been performed for the laminated tubes generated by the process of FIG. 6, and compared to tubes formed by the prior art longitudinal extension method described above. As indicated below, the laminated tube constructed in accordance with the present invention has obviously either similar or superior characteristics, while resulting in a much thinner prosthesis. The characteristics in these tables represent mean values obtained from samples of prior art ePTFE tubes as compared to samples of double layer ePTFE tubes constructed in accordance with this invention:

|  | Prior art PTFE | ePTFE laminate (2-layers) |
|---|---|---|
| Mean ID(mm) | 6.0 | 24 |
| Thickness(mm) | 0.55 | 0.10 |
| Internodal Dist. ($\mu$m) | 17 | 18 |
| Longitudinal Suture retention (g) | 223 | 740 |
| Radial Suture retention (g) | 975 | 213 |
| Radial Tensile Strength (N/mm) | 3.1 | 4.4 |
| Long Tensile Stress(N) | 211 | 195 |
| Balloon Burst Strength (PSI) | 39 | 23.5 |
| Water Entry Pressure (PSI) | 5.5 | 12 |

Figure 8A:
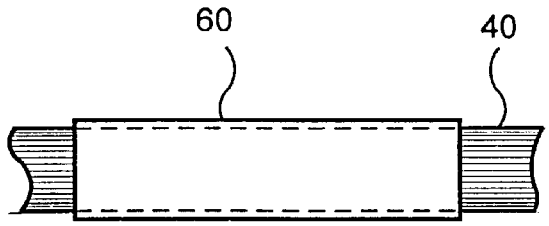

Referring now to FIGS. 8A–8E, a self-expanding prosthesis is made in accordance with this invention as follows. First two tubes 60, 62 are made using the process of FIG. 1. Tube 60 has a nominal inner ID of 24 mm and tube 62 has a nominal inner ID of 26 mm. FIG. 8A shows a 24 mm mandrel with tube 60.

Figure 8B:
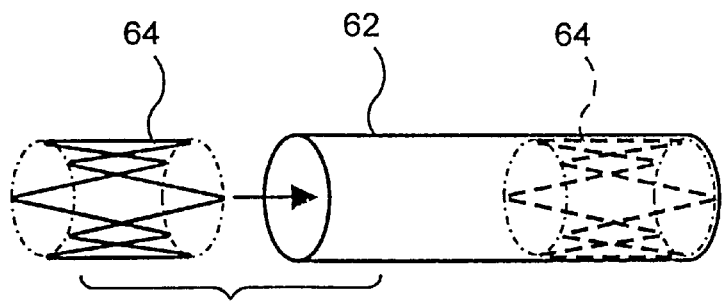

Next, as shown in FIG. 8B, two or more stents 64 are inserted into tube 62 and spaced axially as required. Since the stents have a larger diameter (28 mm), they bias the tube 62 to an open cylindrical configuration. Stents 64 are preferably made of a martensic characteristics which impart memory to the wire. The wire may be, for example, 0.5–1 mm thick and can be made of alloys such as Nitinol.

Figure 8C:
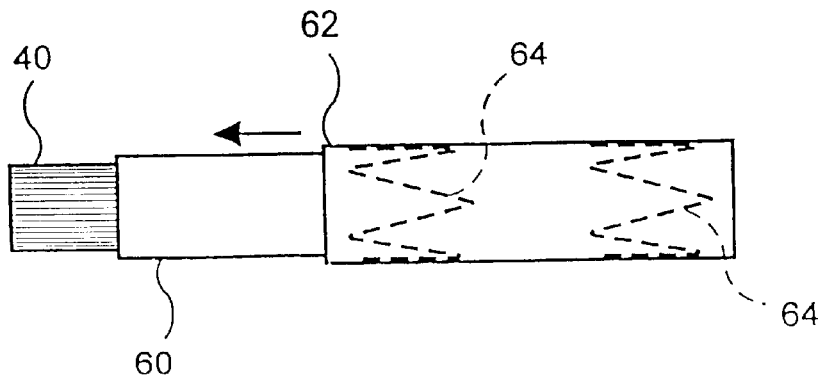

Next, as shown in FIG. 8C, the tube 62 with two stents 64 is inserted over mandrel 40 and tube 60. Once tube 62 is in position over tube 60 with the stents 64 disposed therebetween, wires 66 are wrapped around the ends of the tubes 60, 62 to secure them longitudinally.

Figure 8D:
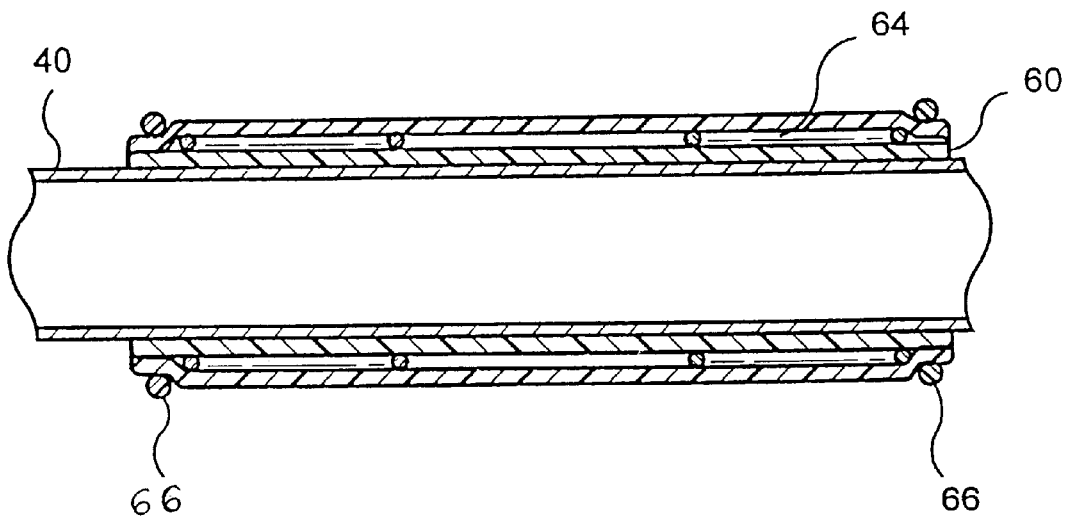
Figure 8E:
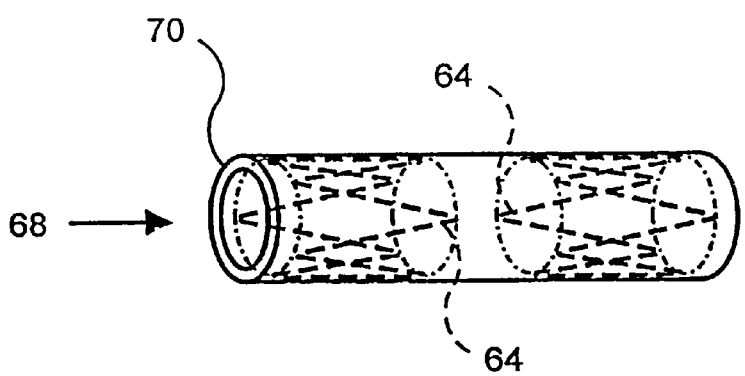

The assembly of FIG. 8D is then put in an oven and heated at 200° C. for about 2 minutes. Again, this causes the two tubes 60, 62 to radially contract and to slightly adhere to each other and to mandrel 40. The assembly is then heated at 360° C. for about ten minutes causing the tubes 60, 62 to be sintered and to form a laminate graft 68 with the wire stents 64 captured in between (FIG. 8E). The wires 66 are cut off and the graft 68 is removed from the mandrel 40 and trimmed.

Since this graft 68 has a nominal outer diameter of about 25 mm, i.e., less than the outer diameter of stents 64, the stents 64 are tensioned radially inwardly, thereby biasing the tubular laminated portion 70 of the graft toward the cylindrical configuration shown in FIG. 8E.

The graft 68 thus produced may be used as a vascular prosthesis to reinforce and/or replace a blood vessel in a patient body. For example, in order to use the graft 68 as a percutaneous endovascular graft, the graft is first collapsed radially. Because the walls of the graft are very thin and the stents 64 are very flexible, the whole graft can be collapsed and reduced radially sufficiently so that it fits into a french size 6 to 20 sheath. The sheath is inserted into the passageway of the vascular system and positioned at the desired location. A flat ended catheter is then used to either push the graft out of the sheath, or maintain the graft in place while the sheath is withdrawn, as described in more detail in U.S. Pat. No. 4,580,568 by Gianturco. Importantly, because the graft 68 is biased to a cylindrical configuration by stent 64, as the graft 68 is ejected from the sheath, it expands automatically radially outward until it engages the inner walls of the respective blood vessel. The graft is selected so that its outer diameter is slightly larger than the inner diameter of the blood vessel, and therefore the biasing force of the stent maintains the graft in place even without suturing. As previously mentioned, some blood vessels have a large inner diameter, in the order of 25 mm or more. Previous grafts could not be made sufficiently large enough and thin enough for blood vessels of this size. However, the process of dilating the PTFE tube taught by the present invention, makes grafts suitable for large diameter blood vessels possible.

Moreover, as discussed, the resulting prosthesis has a high tensile strength and dimensional stability, both axially and radially. The prosthesis further has a high tearing strength so that it is ideally suited for suturing and can resist internal fluid pressures about ten times higher than the nominal requirements.

In the above descriptions, a method is presented for making a stent liner or a graft having a cylindrical shape. Using similar methods but different mandrels, other shapes can be achieved as well, including elliptical or conical shapes. Moreover, two or three of these liners or grafts can be joined to form bifurcated shapes as well.

The methods described can be performed manually or may be automated.

Numerous other modifications may be made to the invention without departing from its scope as defined in the appended claims.

We claim:

1. A vascular prosthesis comprising:
   an inner tube made of ePTFE;
   an outer tube made of PTFE and having an outer tube diameter; and
   a stent formed of a wire and having a cylindrical configuration with a stent diameter, said stent having a relaxed state in which said stent diameter is larger than said outer tube diameter;
   said stent being encapsulated between said inner and outer tubes, said inner and outer tubes cooperating to stress said stent radially inwardly from said relaxed state to a stressed state whereby said prosthesis is biased to a predetermined shape by said stent.

2. The vascular prosthesis of claim 1 wherein said inner and outer tubes are mechanically joined to form a unitary tubular member.

3. The prosthesis of claim 2 wherein said outer tube has a diameter in the range of 10–30 mm.

4. The prosthesis of claim 1 wherein said inner and outer tube have a total thickness in the range of 0.1–0.5 mm.

5. The vascular prosthesis of claim 1 wherein at least one of the inner and outer tubes is formed from an initial tube that has been dilated by repetitively and incrementally expanding the tube in a radial direction until a predetermined diameter is attained.

6. The vascular prosthesis of claim 1 wherein the inner and outer tubes are sintered to form a laminate graft with the stent there between.

7. The vascular prosthesis of claim 1 wherein the wire comprises stainless steel wire.

8. The vascular prosthesis of claim 1 wherein the stent is made of a material exhibiting martensitic characteristics.

9. The vascular prosthesis of claim 1 wherein the wire comprises a nickel-titanium alloy wire.

10. The vascular prosthesis of claim 1 wherein the outer tube has an expanded diameter of greater than 25 mm.

11. The vascular prosthesis of claim 1 wherein the wire has a thickness in a range of approximately 0.5 to 1 mm.

12. The vascular prosthesis of claim 1 wherein both the inner and outer tubes are formed from an initial tube that has been dilated by repetitively and incrementally expanding the tube in a radial direction until a predetermined diameter is attained.

13. The vascular prosthesis of claim 1 wherein the outer tube has a wall thickness of less than 254 mm.

* * * * *